United States Patent

Schick et al.

[11] Patent Number: 5,902,886
[45] Date of Patent: May 11, 1999

[54] METHOD FOR SYNTHESIZING OXETAN-2-ONES AND INTERMEDIATES FOR THEIR PREPARATION

[76] Inventors: Hans Schick; Christine Wedler, both of Chausseestrasse 2 D-10115, D-10115 Berlin, Germany

[21] Appl. No.: 09/008,057

[22] Filed: Jan. 16, 1998

[30] Foreign Application Priority Data

Jan. 23, 1997 [DE] Germany .......................... 197 03 713

[51] Int. Cl.⁶ .................................................. C07D 305/12
[52] U.S. Cl. ............................................................ 549/328
[58] Field of Search .............................................. 549/328

[56] References Cited

FOREIGN PATENT DOCUMENTS

0443449A2  2/1991  European Pat. Off. .
WO94/10133  5/1994  WIPO .

OTHER PUBLICATIONS

P. Barbier, F. Schneider, U.Widmer, *Helv. Chim. Acta*, 1987, 70, 1412–1418.
A. Pommier, J.–M. Pons, P.J. Kocienski, L.Wong, *Synthesis*, 1994, 1294–1300.
N.K. Chadla, A.D. Batcho, P.C. Tank, L.F. Courtney, C.M.Cook, P.M. Wovkulich, M.R.Uskokovic, *J. Org.Chem.*, 1991, 56, 4714–4718.
S. Hanessian, A.Tehim, P.Chen, *J. Org. Chem.* 1993, 58, 7768–7781.
I.Fleming, N.J.Lawrence, *Tetrahedron Lett.*, 1990, 31, 3645–3648.
J.J.Landi, L.M. Garofalo, K.Ramig, *Tetrahedron Lett.*, 1993, 34, 277–280.
P. Barbier, F.Schneider, *J. Org. Chem.*, 1998, 53, 1218–1221.

*Primary Examiner*—Ba K. Trinh
*Attorney, Agent, or Firm*—Collard & Roe, P.C.

[57] ABSTRACT

A method is described for the synthesis of oxetan-2-ones comprising protection of the hydroxy group of an hydroxy ester with an acid-labile acetal protecting group, reduction of this O-protected hydroxy ester to an O-protected hydroxy aldehyde, condensation of this aldehyde with a metal enolate of an activated carboxylic acid derivative and spontaneous deprotection of the hydroxy group during the acidic workup procedure. Using the new O-protected hydroxy aldehydes as intermediates the oxetan-2-ones can be obtained after separation in diastereomerically and enantiomerically pure form, in a remarkably reduced number of steps, and in a significantly improved overall yield.

9 Claims, 2 Drawing Sheets

Reaction Scheme

VIII

IX

X

XI

XII

XIII

Formulas of compounds described in the Examples

METHOD FOR SYNTHESIZING OXETAN-2-ONES AND INTERMEDIATES FOR THEIR PREPARATION

BACKGROUND OF THE INVENTION 3,4-Disubstituted oxetan-2-ones are important intermediates for the preparation of pharmacologically interesting β-lactones, in particular of the enzyme inhibitors lipstatin, tetrahydrolipstatin, esterastin, tetrahydroesterastin, valilactone, panclicin D and structurally related compounds.

Concerning the number of reaction steps, the required starting materials and reagents, the necessary purification steps and/or the overall yield, the hitherto known procedures used for the preparation of these 3,4-disubstituted oxetan-2-ones as enantiomerically and diastereomerically pure compounds are not satisfactory.

The procedure of Barbier, Schneider, and Widmer (P. Barbier, F. Schneider, U. Widmer, *Helv. Chim. Acta* 1987, 70, 1412–1418) for the synthesis of (3S,4S)-3-hexyl-4-[(2R)-2hydroxytridecyl]oxetan-2-one starting from methyl (R)-3-hydroxytetradecanoate affords after six reaction steps an overall yield of 6%.

The procedure of Pommier, Pons, Kocienski, and Wong (A. Pommier, J.-M. Pons, P. J. Kocienski, L. Wong, *Synthesis* 1994, 1294–1300) for the synthesis of the same oxetan-2-one starting from methyl (R)-3-hydroxytetradecanoate affords after five reaction steps an overall yield of 40%. However, there have to be considered three additional steps at the beginning of the synthesis for the preparation of 3-hexyl-3-trimethylsilylketen.

The procedure of Uskokovic et al. (N. K. Chadha, A. D. Batcho, P. C. Tang, L. F. Courtney, C. M. Cook, P. M. Wovkulich, M. R. Uskokovic, *J. Org. Chem.* 1991, 56, 4714–4718) for the synthesis of (3S,4S)-3-hexyl-4-[(2S)-2-hydroxytridecyl]oxetan-2-one (Formula XI) starting from cyclopentadien affords in 17 steps an overall yield of only 1%.

The procedure of Hanessian, Tehim, and Chen (S. Hanessian, A. Tehim, P. Chen, *J. Org. Chem.* 1993, 58, 7768–7781) for the synthesis of (3S,4S)-3-hexyl-4-[(2S)-2-hydroxytridecyl]oxetan-2-one (Formula XI) starting from dodecanal affords in 9 steps an overall yield of 35%.

The procedure of Fleming and Lawrence (I. Fleming, N. J. Lawrence, *Tetrahedron Lett.* 1990, 31, 3645–3648) for (3S,4S)-3-hexyl-4-[(2S)-2-hydroxytridecyl]oxetan-2-one (Formula XI) starting from 3-(dimethylphenylsilyl) propynoic acid affords in 19 steps an overall yield of 10%.

The procedures for the conversion of 2,5-disubstituted β-hydroxy-δ-lactones into the corresponding 3,4-disubstituted oxetan-2-ones according to Ramig et al. (J. J. Landi, L. M. Garofalo, K. Ramig, *Tetrahedon Lett.* 1993, 34, 277–280), Karpf and Zutter (M. Karpf, U. Zutter, European Patent Application 0 443 449 A2, 15.02.1991/28.08.1991), and Barbier and Schneider (P. Barbier, F. Schneider, *J. Org. Chem.* 1988, 53, 1218–1221) are characterized by a high number of reaction steps and consequently by a low overall yield.

The present invention resulted from the intention to develop an efficient procedure for the preparation of oxetan-2-ones for enzyme inhibitors and related compounds with a β-lactone moiety via new intermediates. This procedure should be characterized by a smaller number of reaction steps, the use of easy to introduce and easy to cleave inexpensive protecting groups, and an efficient separation of diastereoisomers.

SUMMARY OF THE INVENTION

In the light of circumstances stated above, the inventors have conducted extensive investigations and, as a result, found that oxetan-2-ones of the general formula I:

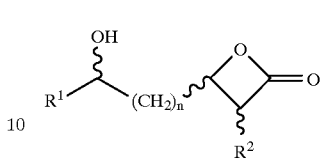

wherein $R^1$, $R^2$, and n are as described below for the general formulas II and VI, respectively, can be prepared in good yields according to the Reaction Scheme in only three steps starting from an ester of a hydroxy acid.

Figure 1:
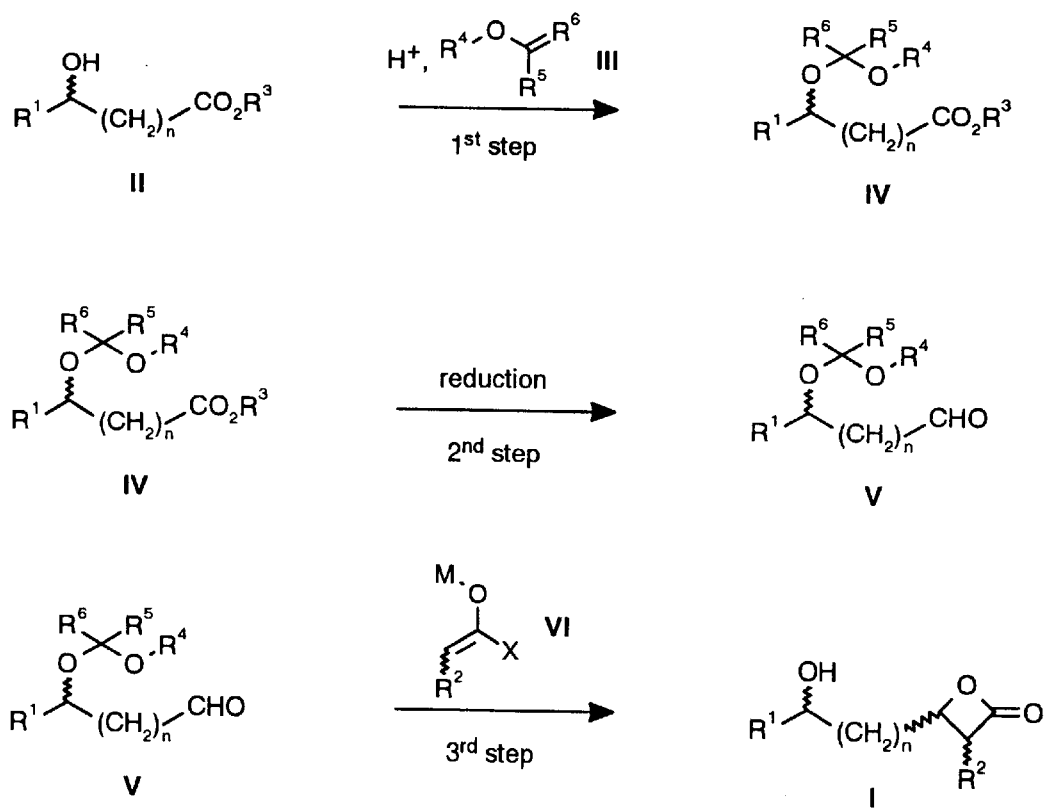
FIG. 1 shows the reaction scheme.
Figure 2:
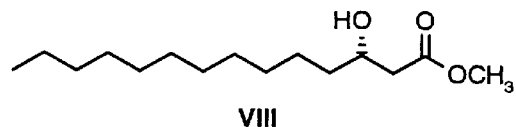
FIG. 2 shows formulas of compounds described in the examples.
Figure 2:
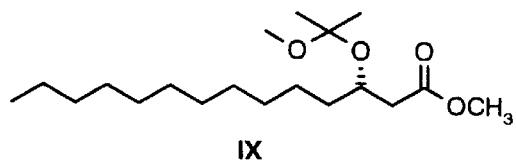
Figure 2:
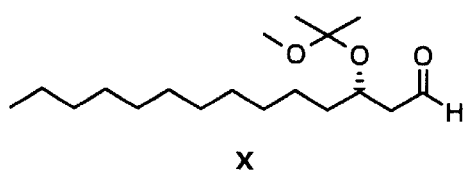
Figure 2:
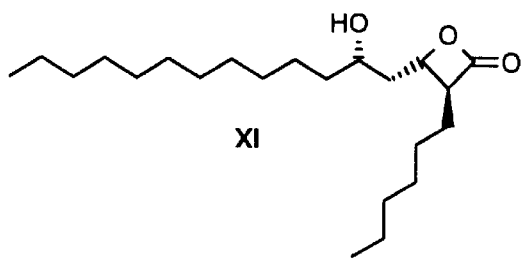
Figure 2:
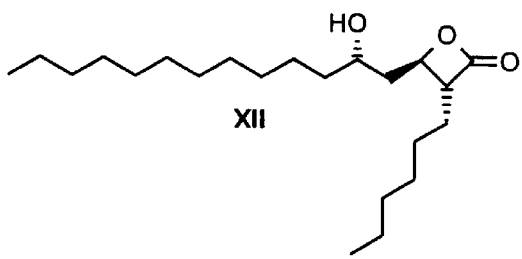
Figure 2:
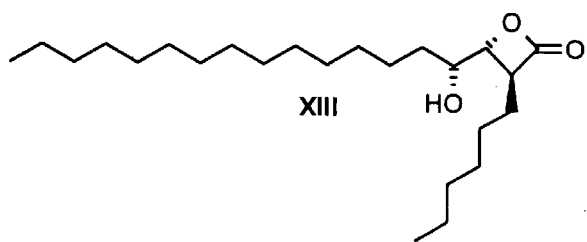

That is, the method involves (a) combining an α- or β-hydroxy ester with an enol ether to an O-protected hydroxy ester, (b) reduction of this O-protected hydroxy ester to an O-protected hydroxy aldehyde, (c) condensation of this O-protected hydroxy aldehyde with a metal enolate of an activated carboxylic acid derivative and spontaneous deprotection during work-up.

DETAILED DESCRIPTION OF THE INVENTION

The alkyl esters of hydroxy acids used in the present method are compounds of the general formula II:

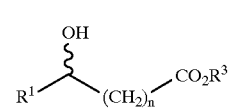

wherein $R^1$ is selected from the group consisting of alkyl, alkenyl, alkadienyl, and alkynyl having from 1 to 20 carbon atoms, in which the carbon chain may be substituted by 1 to 3 halogen atoms, or may be interrupted by an oxygen atom, a sulfur atom or a 1,4-arylene group, or may be substituted by alkyl, aryl or aryl alkyl groups; wherein $R^3$ is an alkyl group having from 1 to 4 carbon atoms; and wherein n is 0 or 1. As used herein, the term alkyl includes saturated, unsaturated, and functionalized carbon chains and rings having straight, branched or cyclic configurations. As used herein, the term aryl includes any aromatic mono- or polycyclic ring system, including benzene, naphthalene, and heteroaromatic ring systems such as pyridine and furan, as well as substituted derivatives of these aromatic and heteroaromatic ring systems.

The enol ethers used in the present method are compounds of the general formula III:

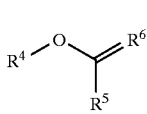

wherein $R^4$ is alkyl, preferably methyl; wherein $R^5$ is selected from the group consisting of H and alkyl, preferably methyl or ethyl; wherein $R^6$ is an alkylidene group, preferably a methylene or an ethylidene group; and wherein $R^5$ and $R^6$ together represent an alkylidene group of the general formula $=CH(CH_2)_m-$, wherein m is an integer between 3 and 14.

The reaction of an alkyl ester of a hydroxy acid of the general formula II with an enol ether of the general formula III is generally carried out in the presence of an acid. Pyridinium p-toluenesulfonate is the preferred acidic catalyst. The reaction is generally carried out in an organic solvent, such as diethyl ether or tetrahydrofuran. It is also possible to use an excess of the enol ether as solvent. The reaction is performed at ambient temperature.

The adduct formed from the reaction of the alkyl ester of a hydroxy acid with an enol ether has the general formula IV:

IV

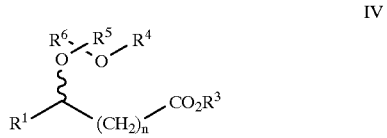

wherein $R^1$, $R^3$, $R^4$, $R^5$, and n are as described above for the general formulas II and III; wherein $R^6$ is alkyl, preferably methyl and ethyl; or wherein $R^5$ and $R^6$ together represent an alkyl chain of the general formula $-(CH_2)_m-$, wherein m is an integer between 4 and 15.

The O-protected hydroxy ester of the general formula IV is reduced in an organic solvent to an O-protected hydroxy aldehyde of the general formula V:

V

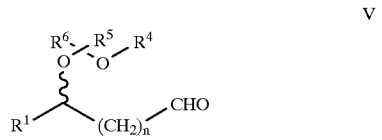

wherein $R^1$, $R^4$, $R^5$, $R^6$, and n are as described above for the O-protected hydroxy ester of the general formula IV.

This reduction is usually performed with diisobutylaluminium hydride in an organic solvent, including toluene and dichloromethane, at a temperature range from about $-80$ to about $-20°$ C.

The aldehyde of the general formula V is combined with a metal enolate of the general formula VI:

VI

wherein $R^2$ is selected from the group consisting of arylamino, alkoxy, aryloxy, alkylsulfanyl, arylsulfanyl, and halogen or from the group consisting of alkyl, alkenyl, alkadienyl, and alkynyl having from 1 to 20 carbon atoms, in which the carbon chain may be substituted by 1 to 3 halogen atoms, or may be interrupted by an oxygen atom, a sulfur atom or a 1,4-arylene group, or may be substituted by alkyl, aryl or aryl alkyl groups; wherein M is selected from the group of mono-, di-, tri-, and tetravalent metals; and wherein X is selected from the group consisting of fluorine, substituted or unsubstituted aryloxy, arylsulfanyl, and heteroaryl. As used herein, the term alkyl includes saturated, unsaturated, and functionalized carbon chains and rings having straight, branched or cyclic configurations. As used herein, the term aryl includes any aromatic mono- or polycyclic ring system, including benzene, naphthalene, and heteroaromatic ring systems such as pyridine and furan, as well as substituted derivatives of these aromatic and heteroaromatic ring systems. Examples for X are phenoxy or 1-benzotriazolyl. Examples for M are Li, MgBr, ZnCl or Ti(OAlkyl)$_3$.

The reaction of the aldehyde of the general formula V with the metal enolate of the general formula VI is usually performed by adding under stirring the aldehyde in an appropriate solvent such as tetrahydrofuran or an dialkyl ether to a solution of the metal enolate of the general formula VI in an appropriate solvent such as tetrahydofuran or an dialkyl ether. The reaction is usually carried out at a temperature between $0°$ C. and $-100°$ C. The reaction is stopped by pouring the reaction mixture into a diluted acid. Stirring at a temperature between 0 and $65°$ C. removes the O-protecting group and affords a mixture of diastereomers of the corresponding 3,4-disubstituted oxetan-2-one of the general formula I:

I

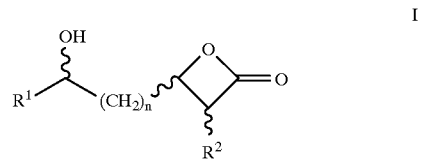

wherein $R^1$, $R^2$, and n are as described above for the general formulas II and VI.

The mixture of diastereomeric oxetan-2-ones of the general formula I obtained by the described method can be separated into diastereomerically pure compounds by physical methods, such as column chromatography and/or recrystallization.

Lithium enolates of the general formula VI (M=Li) are usually prepared from the activated carboxylic acid derivative of the general formula VII:

VII

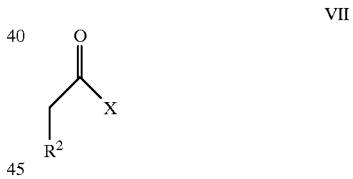

wherein $R^2$ and X are as described above for the general formula VI, by adding the activated carboxylic acid derivative of the general formula VII at an appropriate temperature, e.g. at $-20°$ C., to a solution of a strong base, such as lithium diisopropylamide or lithium hexamethyldisilazide. Other metal enolates of the general formula VI may be prepared from the corresponding lithium enolate by addition of metal salts such as $MgBr_2$, $ZnCl_2$ or $ClTi(OPr^i)_3$.

The invention is further disclosed by the following examples, which are not to be taken as limiting in any way.

EXAMPLES

Example 1

Preparation of methyl (S)-3-(2-methoxyprop-2-oxy) tetradecanoate (IX)

Pyridinium p-toluenesulfonate (90 mg) was added to a solution of methyl (S)-3-hydroxytetradecanoate (VIII, 10.32 g, 40 mmol) in 2-methoxypropen (40 mL). After stirring for 20 min at room temperature the reaction mixture was diluted with diethyl ether (30 mL) and extracted first with a saturated aqueous solution of sodium hydrogen carbonate (3 mL) and then with water (2×2 mL). The combined organic phases were dried (Na$_2$SO$_4$) and concentrated under reduced pressure. The residual colorless oil (13.20 g, 99%) was used in the next step without further purification. $[\alpha]^{25}_D$ +10.01 (c=0.5 in hexane); $^1$H NMR (DMSO-D$_6$) δ 0.86 (t, J=7 Hz, 3H), 1.24–1.27 (m, 26H), 1.44–1.46 (m, 2H), 3.09 (s, 3H), 3.58 (s, 3H), 4.03–4.05 (m, 1H); $^{13}$C NMR (DMSO-D$_6$) δ 13.85, 22.02, 22.05, 24.26, 24.86, 28.67, 28.91, 28.97, 28.98, 29.03, 30.93, 31.27, 35.13, 40.21, 48.46, 51.15, 67.67, 100.35, 171.62. Anal. Calcd for C$_{19}$H$_{38}$O$_4$: C, 69.05; H, 11.59. Found: C, 69.00; H, 11.63.

Starting from ent-VIII or rac-VIII afforded ent-IX and rac-IX, respectively, in the same yield and with the same spectral properties. ent-IX: $[\alpha]^{25}_D$ –8.99 (c=0.5 in hexane).

Example 2

Preparation of (S)-3-(2-methoxyprop-2-oxy) tetradecanal (X)

Diisobutylaluminium hydride (10.7 mL, 60 mmol) dissolved in toluene (30 mL) was precooled to −80° C. and added during 1 h at a temperature of −80° C. to a solution of the crude methyl (S)-3-(2-methoxyprop-2-oxy) tetradecanoate (IX, 13.20 g, 40 mmol) in toluene (100 mL), obtained according to the foregoing described procedure. After complete addition the mixture was stirred for an additional 30 min, diluted with methanol (10 mL), and allowed to warm up to room temperature. A saturated aqueous solution of sodium chloride was added and the precipitate removed by filtration over a pad of fine sand. The filter cake was washed with ethyl acetate (5×15 mL). Filtrate and washings were combined. The aqueous phase was separated and extracted with ethyl acetate (3×20 mL). The combined organic phases were washed with water (10 mL), dried (Na$_2$SO$_4$), and concentrated under reduced pressure. The residual colorless oil (13.7 g, containing still traces of toluene) was used in the next step without further purification. $[\alpha]^{25}_D$ +4.89 (c=0.5 in hexane); $^1$H NMR (DMSO-D$_6$) δ 0.86 (t, J=7 Hz, 3H), 1.24–1.69 (m, 26H), 3.08 (s, 3H), 4.17–4.21 (m, 1H), 9.67 (t, J=2 Hz, 1H), $^{13}$C NMR (DMSO-D$_6$) δ 13.85, 22.05, 24.49, 24.87, 24.96, 28.68, 28.94, 28.97, 29.00, 29.04, 31.28, 35.56, 48.50, 48.93, 66.25, 100.48, 202.80. Anal. Calcd for C$_{18}$H$_{36}$O$_4$: C, 71.95; H, 12.08. Found: C, 72.05; H, 12.28.

Starting from ent-IX and rac-IX afforded ent-X and rac-X, respectively, in the same yield and with the same spectral data. ent-X: $[\alpha]^{25}_D$=−4.43.

Example 3

Preparation and separation of (3S,4S)-3-hexyl-4-[(2S)-2-hydroxytridecyl]oxetan-2-on (XI) and (3R,4R)-3-hexyl)-4-[(2S)-2-hydroxytridecyl]oxetan-2-on (XII)

The crude (S)-3-(2-methoxyprop-2-oxy)tetradecanal (X, 40 mmol) was dissolved in dry THF (10 mL) and cooled to −50° C. The solution was then added within 1 h to a solution of the lithium enolate of 1-octanoyl benzotriazol, maintaining the temperature of the reaction mixture by cooling with a slurry of ethanol in liquid nitrogen at −95 to −100° C. After complete addition the mixture was kept at this temperature for 30 min and allowed to warm up to room temperature overnight. 2N aqueous HCl (50 mL) was added under cooling with ice water and the mixture was stirred for 20 min at 0° C. Diethyl ether (20 mL) was added. The aqueous phase was separated and extracted with diethyl ether (3×25 mL). The organic phase and the extracts were combined, washed with brine (2×20 mL), dried (Na$_2$SO$_4$), and concentrated under reduced pressure. Flash chromatography of the residue on silica gel with hexane/ethyl acetate (4:1) as eluent afforded the more polar oxetan-2-one XI and the less polar oxetan-2-one XII, which were finally purified by recrystallization from pentane/hexane (1:1).

(3S,4S)-3-Hexyl-4-[(2S)-2-hydroxytridecyl]oxetan-2-on (XI): yield 35% [related to methyl (S)-3-hydroxytetradecanoate (VIII)], colorless crystals, mp 63–64° C.; $[\alpha]^{22}_D$ −14.66 (c 0.4 in CHCl$_3$); $^1$H NMR (300 MHz) δ 0.84–0.90 (m, 6H), 1.26–2.07 (m, 33H), 3.28–3.35 (m, 1H), 3.76–3.80 (m, 1H), 4.44–4.50 (m, 1H); $^{13}$C-NMR δ 14.07, 14.17, 22.59, 22.74, 25.52, 26.87, 27.88, 29.02, 29.41, 29.59, 29.63 (2 signals), 29.69, 29.71, 31.57, 31.98, 37.74, 41.24, 56.87, 69.43, 76.39, 171.67. Anal. Calcd for C$_{22}$H$_{42}$O$_3$: C, 74.52; H, 11.94. Found: C, 74.68; H, 11.94.

(3R,4R)-3-Hexyl)-4-[(2S)-2-hydroxytridecyl]oxetan-2-on (XII): yield 5% [related to methyl (S)-3-hydroxytetradecanoate (VIII)], colorless crystals, mp 57–59° C.; $[\alpha]^{22}_D$ 40.74 (c 0.4 in CHCl$_3$); $^1$H NMR (300 MHz, CDCl$_3$) δ 0.86–0.90 (m, 6H), 1.26–1.97 (m, 33H), 3.23–3.29 (m, 1H), 3.74–3.85 (m, 1H), 4.47–4.53 (m, 1H); $^{13}$C-NMR δ 14.07, 14.16, 22.57, 22.73, 25.45, 26.82, 27.76, 29.03, 29.40, 29.55, 29.62 (2 signals), 29.68, 29.70, 31.57, 31.98, 38.18, 41.90, 56.67, 68.62, 75.73, 171.96. Anal. Calcd for C$_{22}$H$_{42}$O$_3$: C, 74.52; H, 11.94. Found: C, 74.66; H, 11.94.

Starting from the aldehydes ent-X and rac-X the oxetan-2-ones ent-XI/ent-XII and rac-XI/rac-XII were obtained in the same yield and with the same spectral data. The mp of ent-XI and ent-XII were the same as those from XI and XII. The optical rotations measured were $[\alpha]^{22}_D$ +14.87 (c 0.4 in CHCl$_3$ for ent-XI) and $[\alpha]^{22}_D$ −36.65 (c 0.4 in CHCl$_3$ for ent-XII). The mp of rac-XI and rac-XII were 49–50 and 44–46° C., respectively.

Example 4

Preparation of (3RS,4SR)-3-hexyl-4-[(1SR) 1-hydroxypentadecyl]oxetan-2-one (rac-XIII)

Starting from methyl (R,S)-2-hydroxyhexadecanoate (5.73 g, 20 mmol) (3RS,4SR)-3-hexyl-4-[(1SR)-1-hydroxypentadecyl]oxetan-2-one (rac-XIII) was obtained in a reaction sequence in full analogy to the examples 1–3. rac-XIII is a colorless, crystalline compound having a mp of 40–41° C. $^1$H-NMR (500 MHz, CDCl$_3$) δ 0.86–0.91 (m, 6 H), 1.23–1.57 (m, 35H), 1.65–1.76 (m, 1 H), 1.79–1.87 (m, 1 H), 3.60–3.65 (m, 1 H), 3.97–4.02 (m, 1H), 4.14–4.16 (m, 1 H); $^{13}$C-NMR (125 MHz, CDCl$_3$) δ 14.00, 14,09, 22,51, 22.68, 25.45, 26.97, 27.68, 28.91, 29.34, 29.45 (2 signals), 29.54, 29.61, 29.64–29.67 (4 signals), 31.50, 31.91, 32.11, 50.55, 69.80, 79.29, 171.29.

We claim:

1. A method for the synthesis of oxetan-2-ones comprising the steps of (a) combining a hydroxy ester of the general formula II:

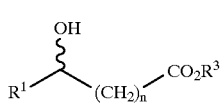

II wherein R$^1$ is selected from the group consisting of alkyl, alkenyl, alkadienyl, and alkynyl having from 1 to 20 carbon atoms, in which the carbon chain may be substituted by 1 to 3 halogen atoms, or may be interrupted by an oxygen atom, a sulfur atom or a 1,4-arylene group, or may be substituted by alkyl, aryl or aryl alkyl groups;

wherein $R^3$ is an alkyl group having from 1 to 4 carbon atoms;

and wherein n is 0 or 1, with an enol ether of the general formula III:

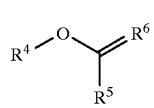

III wherein $R^4$ is alkyl, preferably methyl;
wherein $R^5$ is selected from the group consisting of H and alkyl, preferably methyl or ethyl;
wherein $R^6$ is an alkylidene group, preferably a methylene or ethylidene group;
and wherein $R^5$ and $R^6$ together represent an alkylidene group of the general formula $=CH(CH_2)_m-$, wherein m is an integer between 3 and 14, to an adduct of the general formula IV:

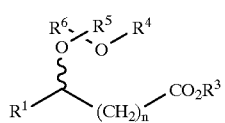

IV wherein $R^1$, $R^3$, $R^4$, $R^5$, and n are as described above for the general formulas II and III;
wherein $R^6$ is alkyl, preferably methyl or ethyl;
or wherein $R^5$ and $R^6$ together represent an alkyl chain of the general formula $-(CH_2)_m-$, wherein m is an integer between 4 and 15, (b) reduction of this adduct to an O-protected hydroxy aldehyde of the general formula V:

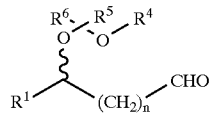

V wherein $R^1$, $R^4$, $R^5$, $R^6$, and n are as described above for the adduct of the general formula IV, (c) and condensation of this aldehyde with a metal enolate of the general formula VI:

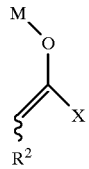

VI wherein $R^2$ is selected from the group consisting of arylamino, alkoxy, aryloxy, alkylsulfanyl, arylsulfanyl, and halogen or from the group consisting of alkyl, alkenyl, alkadienyl, and alkynyl having from 1 to 20 carbon atoms, in which the carbon chain may be substituted by 1 to 3 halogen atoms, or may be interrupted by an oxygen atom, a sulfur atom or a 1,4-arylene group, or may be substituted by alkyl, aryl or aryl alkyl groups;

wherein M is selected from the group of mono-, di-, tri-, and tetravalent metals;

and wherein X is selected from the group consisting of fluorine, substituted or unsubstituted aryloxy, arylsulfanyl, and heteroaryl, preferably phenoxy and 1-benzotriazolyl, to O-protected intermediates, which are hydrolyzed during the acidic workup to oxetan-2-ones of the general formula I:

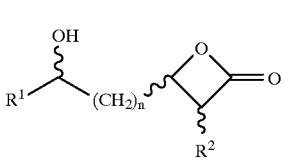

I wherein $R^1$, $R^2$, and n are as described above for the general formulas II and VI, and (d) separation of the mixture of diastereomeric oxetan-2-ones of the general formula I into diastereomerically pure compounds by physical methods such as chromatography and/or recrystallization.

2. The method of claim 1 wherein the oxetan-2-ones of the general formula I are obtained as racemic or enantiomerically pure compounds.

3. The method of claim 1 wherein a compound of the general formula II is condensed with 2-methoxypropen in the presence of pyridinium p-toluenesulfonate with or without an organic solvent at a temperature between −20 and +30° C., preferably at a temperature of 20–25° C.

4. The method of claim 1 wherein the reduction of an O-protected hydroxy ester of the general formula IV is performed with diisobutylaluminium hydride in toluene or dichloromethane at a temperature between −20 and −90° C.

5. The method of claim 1 wherein the condensation of the aldehyde of the general formula V with a metal enolate of the general formula VI is performed at a temperature between −20 and −100° C.

6. The method of claim 1 wherein M of the metal enolate of the general formula VI is Li, MgBr, ZnCl or Ti(OPr$^i$)$_3$.

7. The method of claim 1 wherein $R^1$ is $C_{11}H_{23}$, $R^2$ is $C_6H_{13}$, and n is 1.

8. The method of claim 1 wherein $R^1$ is $C_5H_{11}$, $R^2$ is $C_6H_{13}$, and n is 1.

9. The method of claim 1 wherein $R^1$ is $C_7H_{15}$, $R^2$ is $C_{10}H_{21}$, and n is 1.

* * * * *